(12) United States Patent
Peppas et al.

(10) Patent No.: US 8,304,247 B2
(45) Date of Patent: Nov. 6, 2012

(54) RECOGNITIVE HYDROGEL

(75) Inventors: Nicholas A. Peppas, Austin, TX (US); Carolyn Bayer, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 154 days.

(21) Appl. No.: 12/581,308

(22) Filed: Oct. 19, 2009

(65) Prior Publication Data
US 2010/0151580 A1 Jun. 17, 2010

Related U.S. Application Data

(63) Continuation of application No. PCT/US2008/060662, filed on Apr. 17, 2008.

(60) Provisional application No. 60/912,380, filed on Apr. 17, 2007.

(51) Int. Cl.
*G01N 27/02* (2006.01)
*G01N 27/00* (2006.01)

(52) U.S. Cl. ........... 436/86; 436/149; 436/94; 73/61.62; 73/61.41; 73/53.01; 435/7.1; 435/4

(58) Field of Classification Search .................. 436/149, 436/49; 73/61.62, 61.41, 53.01; 435/7.1, 435/4; 424/423, 400, 78.27, 78.26, 78.17, 424/78.08
See application file for complete search history.

(56) References Cited

U.S. PATENT DOCUMENTS

| 6,224,893 | B1 * | 5/2001 | Langer et al. ................. 424/423 |
| 2004/0007051 | A1 * | 1/2004 | Bashir et al. ................. 73/61.62 |
| 2004/0126814 | A1 * | 7/2004 | Singh et al. .................... 435/7.1 |
| 2007/0122829 | A1 * | 5/2007 | Ballerstadt et al. ............... 435/6 |

FOREIGN PATENT DOCUMENTS

| WO | WO 2006/099248 | * | 9/2006 |
| WO | WO 2006/116734 | * | 11/2006 |

* cited by examiner

*Primary Examiner* — Christine T Mui
(74) *Attorney, Agent, or Firm* — Baker Botts L.L.P.

(57) ABSTRACT

Novel recognitive hydrogels and sensors are provided, as well as methods of fabricating and using such hydrogels and sensors. Such recognitive hydrogels may comprise a molecularly imprinted polymer having a binding cavity specific for a triggering molecule and a conductive polymer associated with the molecularly imprinted polymer. Such sensors may comprise the recognitive hydrogels and an impedance sensing component. Such methods may comprise providing a triggering molecule, providing a sensor comprising a molecularly imprinted polymer having a binding cavity specific for the triggering molecule, a conductive polymer associated with the molecularly imprinted polymer, and an impedance sensing component, introducing the triggering molecule into the sensor, and detecting a change in impedance of the recognitive hydrogel with the impedance sensing component.

22 Claims, 13 Drawing Sheets

RECOGNITIVE HYDROGEL

CROSS-REFERENCE TO RELATED APPLICATIONS

This application is a continuation of International Application No. PCT/US2008/060662 filed Apr. 17, 2008, which claims the benefit of U.S. Provisional Patent Application Ser. No. 60/912,380, filed Apr. 17, 2007, the entire disclosure of which is hereby incorporated by reference.

STATEMENT OF GOVERNMENT INTEREST

The present disclosure was made with support under Grant Number DGE-0333080 awarded by National Science Foundation. The U.S. government has certain rights in the invention.

BACKGROUND

The present invention relates to recognitive hydrogels, recognitive polymers and inherent signal transduction. In particular, the present invention relates to combinations of molecularly imprinted polymers and conductive polymers.

Molecularly imprinted polymers (MIPs) are polymers that are formed in the presence of an imprinted compound such that the imprinted compound may be later removed, leaving a MIP that is able to recognize and bind to the imprinted compound via a binding cavity. MIPs with various specificities have been developed. The ability of MIPs to specifically recognize other compounds is difficult to exploit in a commercially useful manner unless there is a way to detect binding of the imprinted compound to the MIP in a sample.

Transduction of a MIP/imprinted compound binding event has been demonstrated optically and via a quartz crystal microbalance, but each of these techniques would be difficult to use in a clinical diagnostic test. Optical detection would require extensive sample preparation because typical clinical samples (such as blood) are opaque and do not naturally lend themselves to optical detection methods. Quartz crystal microbalances are expensive to manufacture, prohibiting disposable tests and introducing sample cross contamination issues, and also require relatively large sample volumes.

Conductive polymers (CPs) are macromolecules which are able to conduct an electrical charge. This ability to conduct a charge may be altered, for example, if the chemistry of the CP is altered. Many CPs are responsive to oxidation-reduction (redox) reactions and are thus useful in electrochemical sensors, but redox reactions are limited to molecules which can react, typically in the presence of a catalyst or enzyme. CPs have been used in a variety of electrochemical reactions. For example, polyelectrolyte CPs demonstrate "super-quenching" of fluorescence in the presence of a biomolecule in solution due to disruption of the charge by the biomolecule. CPs have been combined with hydrogels to detect electrochemical signals.

Many molecules exist, however, which do not participate in redox reactions and/or are not enzymatically active. Detection of these molecules is also significant. Further, detection of molecules that do participate in redox reaction in other fashions may provide alternative sensors. While limited experiments involving the mixture of MIPs able to detect one type of biomolecule and CPs have been performed, the functionality of such a system and the ability to actually detect the molecule has not been well-explored.

DRAWINGS

The following figures form part of the present specification and are included to further demonstrate certain aspects of the present invention. The invention may be better understood by reference to one or more of these drawings in combination with the description of embodiments presented herein.

Figure 1:
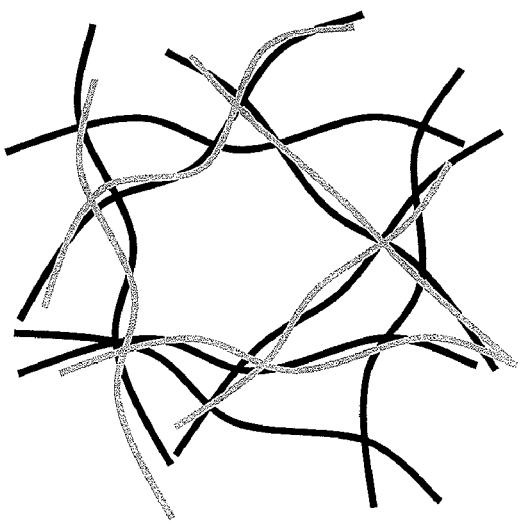
FIG. 1 illustrates a recognitive hydrogel according to an embodiment of the present invention.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

In certain embodiments, the present disclosure provides a recognitive hydrogel comprising a molecularly imprinted polymer having a binding cavity specific for a triggering molecule and a conductive polymer associated with the molecularly imprinted polymer.

In certain embodiments, the present disclosure provides a sensor comprising (a) a recognitive hydrogel comprising (1) a molecularly imprinted polymer having a binding cavity specific for a triggering molecule and (2) a conductive polymer associated with the molecularly imprinted polymer, and (b) an impedance sensing component.

In certain embodiments, the present disclosure provides a method comprising providing a triggering molecule, providing a sensor comprising a molecularly imprinted polymer having a binding cavity specific for the triggering molecule, a conductive polymer associated with the molecularly imprinted polymer, and an impedance sensing component, introducing the triggering molecule into the sensor, and detecting a change in impedance of the recognitive hydrogel with the impedance sensing component.

As used herein, the term "associated" and its derivatives is defined to mean any suitable means of linking one or more entities which does not adversely affect either entity or the resulting product. Such linking may be physical or chemical. Examples of suitable linking include, but are not limited to, copolymerization and semi-interpenetrating network polymerization.

A variety of molecularly imprinted polymers (MIPs) may be useful in the compositions and methods of the present invention. Such MIPs include, but are not limited to, configurationally biomimetic imprinted polymers (CBIPs). CBIPs are a particular type of MIP that are able to very specifically recognize a type of imprinted compound: the triggering molecule. The previous works of Nicholas Peppas and colleagues include U.S. Patent Application Publication No. 2007/0071712 published Mar. 29, 2007, PCT Application Publication No. WO 2008/039920 published Apr. 3, 2008, U.S. Patent Application Publication No. 2007/0190084 published Aug. 16, 2007, and PCT Application Serial Number PCT/US2007/83362 filed Nov. 1, 2007, the entire disclosures of which are hereby incorporated by reference. Some advantages of certain MIPs may include their physical and chemical stability, low cost of fabrication, and their ability to be customizable to many applications.

MIPs suitable for use in the compositions and methods of the present invention include polymers that can selectively sense, for example, through recognition, detection and binding, a triggering molecule which was present when the MIP was formed and later removed. This triggering molecule may be any of a variety of compounds of interest which is capable of being selectively recognized by the MIP. In certain embodiments, the triggering molecule may comprise one or more of a carboxyl functional group, hydroxyl functional group, amino functional group, carbonyl functional group, thiol functional group, and other similar functional groups. In certain embodiments, the triggering molecular may be a biomolecule, including, but not limited to, a protein, a polypeptide, a peptide, a carbohydrate (such as a monosaccharide, an oligosaccharide, or a polysaccharide), a glycoprotein, a proteoglycan, or any other suitable biological molecule. In certain embodiments, the triggering molecule may be a medically relevant compound, including, but not limited to, glucose, serotonin, C-reactive protein, a virus, or a cell. In certain embodiments, the triggering molecule may also be a molecular decoy or moiety such as glucose, a phenol, a polyacid, a polyol, a polyamine, a polypeptide, or similar molecules. In certain embodiments, the molecular decoy may be attached to a second compound, among other things, to allow easier formation of the MIP or detection of this second compound than if the second compound itself were used as a triggering molecule. MIPs may detect triggering molecules of a variety of sizes, including molecules of a size from about 1 nm to about 1 μm.

MIPs may be synthesized by free radical polymerization of any monomer and crosslinking agent able to form an MIP having at least one binding cavity for the triggering molecule. To form the MIP, the monomer and crosslinking agent may be brought together in the presence of the triggering molecule. After polymerization, the triggering molecule is removed without destroying the MIP. Suitable polymerization methods may include, but are not limited to, free radical polymerization, anionic polymerization, cationic polymerization, stereospecific (Ziegler Natta) polymerization, or atom transfer radical polymerization (ATRP). The MIP retains a binding site able to bind and thus sense the triggering molecule. The binding site typically exhibits specificity to the triggering molecule. In certain embodiments, the binding site may be highly specific such that it can distinguish between two very similar triggering molecules, such as glucose and fructose or polypeptides differing by only one amino acid. In certain embodiments, the specificity of the MIP may be such that it is biomimetic, that is, it mimics the recognition abilities of a biological molecule or pathway, such as an antibody. In certain embodiments, MIPs may be made and/or used in the form of hydrogel networks, gels, or polymers.

Suitable monomers to form MIPs useful in the compositions and methods of the present invention may include, but are not limited to, acrylic acid, methacrylic acid, ethacrylic acid, propacrylic acid, various acrylates, methacrylates, and acrylamides. Derivatives of these compounds may also be suitable. The term "derivative," as used herein, includes any compound that is made from one of the listed compounds, for example, by replacing one atom in the listed compound with another atom or group of atoms, rearranging two or more atoms in the listed compound, ionizing one of the listed compounds, or creating a salt of one of the listed compounds. In certain embodiments, the MIPs useful in the compositions and methods of the present invention may be formed from more than one monomer and thus may be a copolymer. The term "copolymer," as used herein, is not limited to polymers comprising two types of monomeric units, but includes any combination of monomeric units, e.g., terpolymers, tetrapolymers, and the like.

Suitable crosslinking agents include, but are not limited to, ethylene glycol dimethacrylate, diethylene glycol dimethacrylate, triethylene glycol dimethacrylate, tetraethylene glycol dimethacrylate, poly(ethylene glycol dimethacrylate), bisacrylamides and divinyl benzene. Derivatives of these compounds may also be suitable. These crosslinking agents may contain between 5 and 100 units, specifically between about 5 and 25 units and more specifically between about 5 and 10 units.

Typically, a conductive polymer (CP) may be a chain of smaller molecules that is able to conduct an electrical charge along at least a portion of its length. CPs suitable for use in the compositions and methods of the present invention may include, but are not limited to, active conductive materials such as polyaniline (PANI), polypyrrole, polythiophene, and polyacetylene. Derivatives and/or copolymers of these materials may also be suitable. In certain embodiments, CPs such as PANI may be doped in order to become conductive materials. Doping occurs when, for example, the conductive polymer is exposed to an acid. By way of explanation, and not of limitation, the hydrogen ions from the acid associate with electropositive sections of the CP, forming an additional electronic charge transfer state, referred to as a polaron. These polarons then allow the conduction of current through a CP. In certain embodiments, the hydrogen ions can be donated by a polymer acid or a small molecule acid. Donating hydrogen atoms by a polymer acid, among other things, may increase the CP solubility and dopant stability. Polyelectrolytes with basic qualities may also be used to dope the conductive polymer and create the same advantages.

Conductive polymers are typically sensitive to ionic compounds. As a result, ionic compounds may interfere with the function and specificity of the recognitive hydrogel. To reduce this effect, the recognitive hydrogel, in certain embodiments, may include a second polyelectrolyte that is complementary in charge to the doping polyelectrolyte.

In certain embodiments, the recognitive hydrogels of the present invention (also called recognitive/conductive copolymer hydrogels or RECONGELs) may physically link one or more MIPs and one or more CPs. In particular, the recognitive hydrogels may contain chemically linked copolymers or physically mixed composites of the one or more CPs and the one or more MIPs, or a combination thereof. Recognitive hydrogels may be formed by copolymerization, interpenetrating network polymerization, or a combination of these two methods. In certain embodiments, one or more MIPs may be formed in the same manner as MIP hydrogel networks, but with the addition of one or more CPs.

In certain embodiments, the MIPs in the recognitive hydrogels of the present invention may use non-covalent bonding to form a specific interaction between the triggering molecule and the recognitive hydrogel. The recognitive hydrogel may have a high degree of crosslinking and/or a low swelling ratio to reduce deformation of the binding cavity of the MIP and thus preserve MIP binding specificity.

In certain embodiments, the recognitive hydrogels may be formed by co-forming the MIP and the CP (e.g. by copolymerization of the monomers), rather than by mixing previously formed polymers of one or both of these components. For example, the monomer(s) of the MIP and the monomer(s) of the CP (or in an alternative embodiment the CP polymer), along with appropriate crosslinking agents and the triggering molecule, may be combined in a manner appropriate to form a MIP with a binding cavity for the triggering molecule and associated with the CP.

In certain embodiments, the recognitive hydrogel may contain more than one type of MIP, each specific to a different triggering molecule. In certain embodiments, the different MIPs may have a different effect on the impedance of the hydrogel, allowing the different triggering molecule to be distinguished by the same recognitive hydrogel. It should be noted that a change in impedance may be manifested by a measured change in the resistance or conductance of the hydrogel. Whereas resistance is a measure of an object's ability to retard the passage or flow of an electrical current, and conductance is the inverse of that same measure, impedance is a measure of opposition to time-varying electric current, or phase.

In certain embodiments, the recognitive hydrogels of the present invention may experience a change in impedance. In certain embodiments, such an impedance change may depend upon the amount of triggering molecule bound to the recognitive hydrogel. This change in impedance may occur in one or more of at least three different ways. First, when the triggering molecule binds to the MIP, it may alter the local ionic concentration within the recognitive hydrogel, thereby causing a change in the ionic conductance of the hydrogel. Second, when the triggering molecule binds to the MIP, it may change conductance pathways in the recognitive hydrogel, thereby causing a change in the electronic conductance of the hydrogel. Third, when the triggering molecule binds to the MIP, it may cause a change in the conformation of the network which induces a change in the electronic conductance of the hydrogel. Both a change in ionic conductance and a change in electrical conductance can be measured, and both may result in a change in impedance of the recognitive hydrogel.

Any method suitable for use with and capable of measuring a change in impedance of the recognitive hydrogels of the present invention may be used for such a measurement. Examples of suitable methods include, but are not limited to, use of a biomolecule impedance analyzer (such as the Agilent impedance analyzers and enhanced impedance analyzers), or other similar biological impedance analyzers (BIAs). In addition, other methods may be used, such as the use of AC impedance sensing devices, bio-impedance sensing devices (BISDs), electric cell-substrate impedance sensing (ECIS), or non-contact impedence sensing surfaces. One or ordinary skill in the art, with the benefit of this disclosure, may recognize additional methods for measuring a change in impedance of the recognitive hydrogels of the present invention. Such methods are considered to be within the spirit of the present disclosure.

In certain embodiments, the CP in the recognitive hydrogel is a conjugated polymer, i.e. it has alternating double bonds. The CP is associated with the CBIP so that components of the MIP form at least part of the conductive pathway through the hydrogel.

In certain embodiments, the molecularly imprinted polymer may change conformation upon exposure to the triggering molecule. Examples of such conformational changes include, but are not limited to, the dissociation of the molecularly imprinted polymer from the conductive polymer, or a change in hydrophilicity or hydrophobicity which may lead to swelling or deswelling of one or more of the polymers in the recognitive hydrogel. In certain embodiments, this conformational change may result in a change in the charge transport properties of the conductive polymer.

In certain embodiments, the recognitive hydrogel may provide charge transport properties to the CP, for example by doping the CP as shown in FIG. 1. The doping of the CP may occur, for example, by introduction of a polyelectrolyte during the synthesis of the recognitive hydrogel. The dopant charges may provide charge mobility, and therefore conductive properties, to the recognitive hydrogel. Binding of the imprinting compound to the recognitive hydrogel may cause dedoping of the conductive polymer, as the association between the polyelectrolyte of the recognitive hydrogel may change the dopant charges available to the CP. In certain embodiments, when the MIP binds to the triggering molecule, the delocalized charges of the associated CP will be disturbed, dramatically changing the conductance of the recognitive hydrogel.

Figure 2:
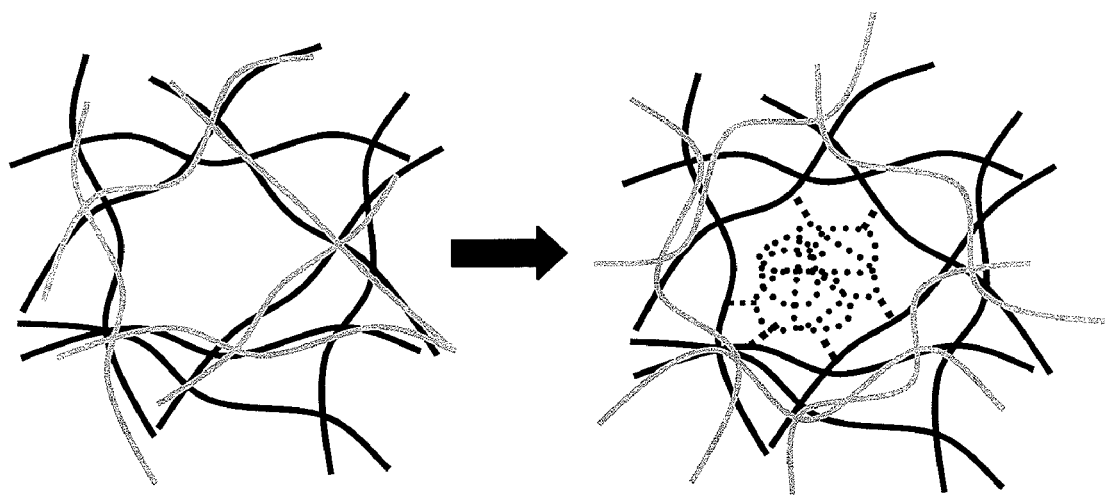
FIG. 2 illustrates the effects of triggering molecule binding on CP doping, according to an embodiment of the present invention.

In certain embodiments, the triggering molecule may induce a change in the doping of the CP by a close interaction between the MIP and the CP, as shown in FIG. 2. In certain embodiments, the hydrogel material may be synthesized so that the doping of the CP is provided by the MIP itself. Thus, in the presence of a triggering molecule, the charge delocalization on the CP chain or the association between the dopant polymer and the CP chain may be disrupted. The impact of this disruption may be detected by measuring the conductivity of the recognitive hydrogel.

In a specific embodiment, the CP and MIP may change conformation relative to each other, leading to a change in conductivity of the recognitive hydrogel. The presence of a triggering molecule may impact the degree of swelling of the recognitive hydrogel, which may cause a corresponding change in the conductivity of the recognitive hydrogel.

Because of these and other properties, the recognitive hydrogels of the present invention, in certain embodiments, may be used as a component of an assay device or material. They may be used in any application that benefits from recognition of particular compounds, including clinical diagnostics, military applications, environmental detoxification, and also in consumer products, and other similar uses. Recognitive hydrogels may be useful functional components in micro- and nanodevices due to the ease with which their recognition and actuation properties can be precisely tailored. The recognitive hydrogels of the present invention, including environmentally responsive MIP hydrogels and biomimetic polymer networks, may be used as sensing/recognition elements in novel diagnostic devices, such as microsensors and microarrays, and therapeutic devices, for tailoring loading and release properties.

For example, the recognitive hydrogels of the present invention may be integrated into medical or pharmaceutical microdevices, a film on a silicon wafer, a microcantilever, a glass slide, a polymer film or substrate, a biodegradable polymer substrate, or other such devices and materials. For integration of these recognitive hydrogels at the micro-/nanoscale, precise spatial control of patterning may be used. For example, recognitive hydrogels of the present invention may also be used in association with photolithography processes to create biosensors with sensing/recognitive capabilities as well as signal transmission capabilities. A mask aligner may be used in the photolithography process to enable precise micropatterning of ultra-thin polymers films via UV free-radical polymerization. In another example, an organosilane coupling agent may be used to pattern recognitive hydrogels of the present invention onto inorganic silicon substrates. The coupling agent may cause covalent adhesion between the dissimilar polymer network and the silicon surface.

In certain embodiments, the recognitive hydrogels of the present invention may be patterned onto a microcantilever. Microcantilevers have been demonstrated to be capable of sensing nanomechanical forces. Microcantilevers can also be designed to bend in response to applied current in a piezoelectric device format. The addition of a recognitive hydrogel to a microcantilever may provide additional information that allows a quantitative measurement from a microcantilever-based sensor because the recognitive hydrogel may be adhered to the microcantilever itself. The degree of bending of the microcantilever may directly reflect the amount of triggering molecule bound to the recognitive hydrogel.

In certain embodiments, the recognitive hydrogels of the present invention may be used to detect specific proteins or peptides. The field of proteomics has expanded the number of target proteins that are clinically relevant. Scientists are finding that the disease states of the body are often regulated by proteins or peptides, and the detection of minute amounts of the relevant molecules via a MIP biosensor, microdevice or nanodevice may aid in the detection of disease. In one example, a protein sensing device, developed using microfabrication technologies, may include an array for sensing multiple proteins at once, as would a protein microarray. In contrast to most protein microarrays, a microarray using the recognitive hydrogels of the present invention, among other things, may avoid the pitfalls of antibody development and stability.

Other specific embodiments use recognitive hydrogels as sensing elements in biosensors, intelligent drug delivery devices, and systems for immunoassays. In comparison to biological entities, biomimetic polymer networks are advantageous because they can be designed to mimic biological recognition pathways and at the same time exhibit other abiotic properties that are more favorable, such as greater stability in harsh environments.

To facilitate a better understanding of the present invention, the following examples of specific embodiments are given. In no way should the following examples be read to limit or define the entire scope of the invention.

EXAMPLES

Example 1

Hydrogel 1

In the first hydrogel, a polyacid templated polyaniline (PANI) synthesized using previously published methods (Yoo, 2007), was blended with a CBIP solution and then UV polymerized to create one type of semi-interpenetrating polymer network (IPN) recognitive hydrogel.

A PANI-poly(2-acrylamido-2-methyl-1-propane-sulfonic acid) (PAAMPSA) recognitive hydrogel was made by blending PANI-PAAMPSA monomers, and then UV polymerizing the material to form a film. PANI is a conjugated polymer which is conductive in its protonated emeraldine salt form. PANI can be synthesized on PAAMPSA to generate a complex which demonstrates improved solubility. The PAAMPSA in this complex acts both as a dopant and a stabilizer. Preparation of glass substrates was accomplished by first cleaning the substrates with solvent, followed by a Pirhana clean, then exposing the glass to a solution of 3-methacryloxypropyltrimethoxysilane (γ-MPS) in acetone. After exposure to γ-MPS, the slides were rinsed in acetone, then in methanol, and then dried with nitrogen. PANI-PAAMPSA was obtained as a dry powder from Dr. Yueh-Lin Loo at UT Austin. PANI-PAAMPSA was synthesized as described in Lee, K. S., App Phys Lett, 2005, 86(7): p. 074102. To form an interpenetrating hydrogel-CP network (a type of recognitive hydrogel), the PANI-PAAMPSA was first prepared by weight percentage in deionized water. The CBIP monomers, acrylamide and methacrylic acid with polyethylene glycol dimethacrylate crosslinker was added to the PANI-PAAMPSA solution. 1-hydroxycyclohexyl phenyl ketone was added as the UV free radical initiator for the polymerization and the entire solution was sonicated. The solution was pipetted into glass slide "sandwich" with a spacer. One slide of the sandwich was treated with γ-methacryloxypropyl trimethoxysilane silane for adhesion.

Figure 3:
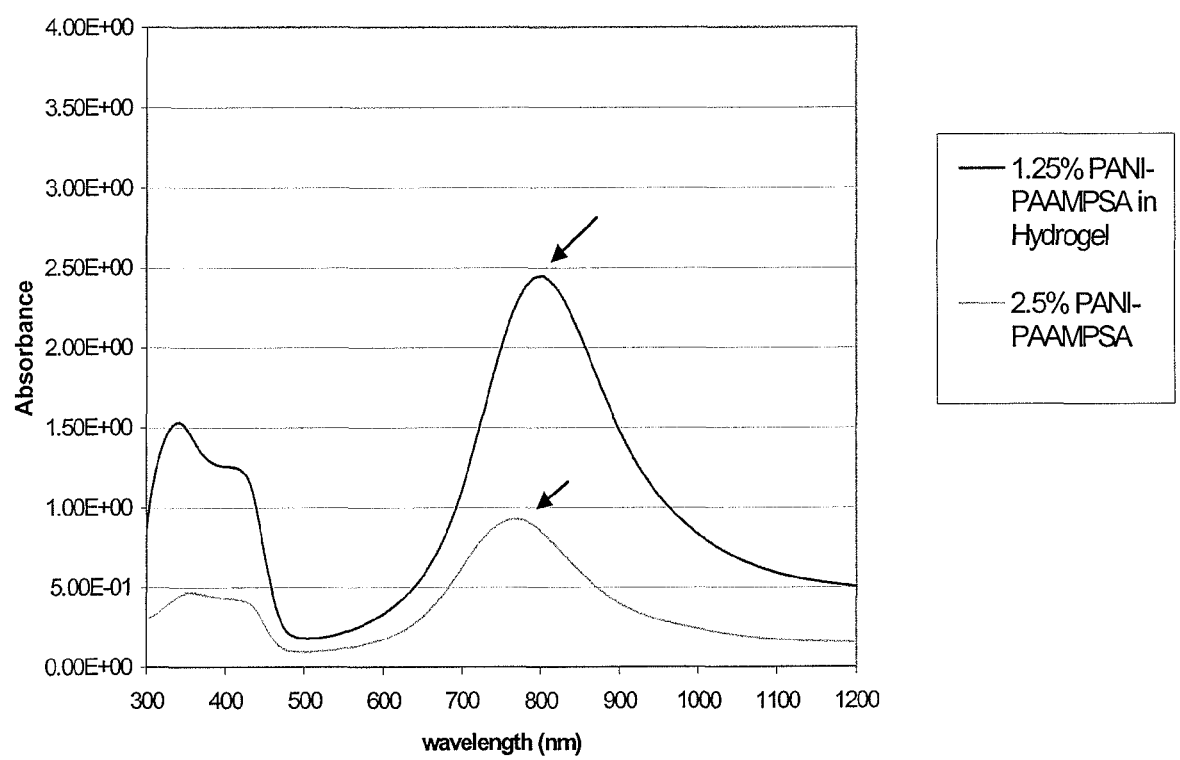
FIG. 3 illustrates the absorbance of a film containing PANI-PAAMPSA alone or in a recognitive hydrogel, according to an embodiment of the present invention.
Figure 4:
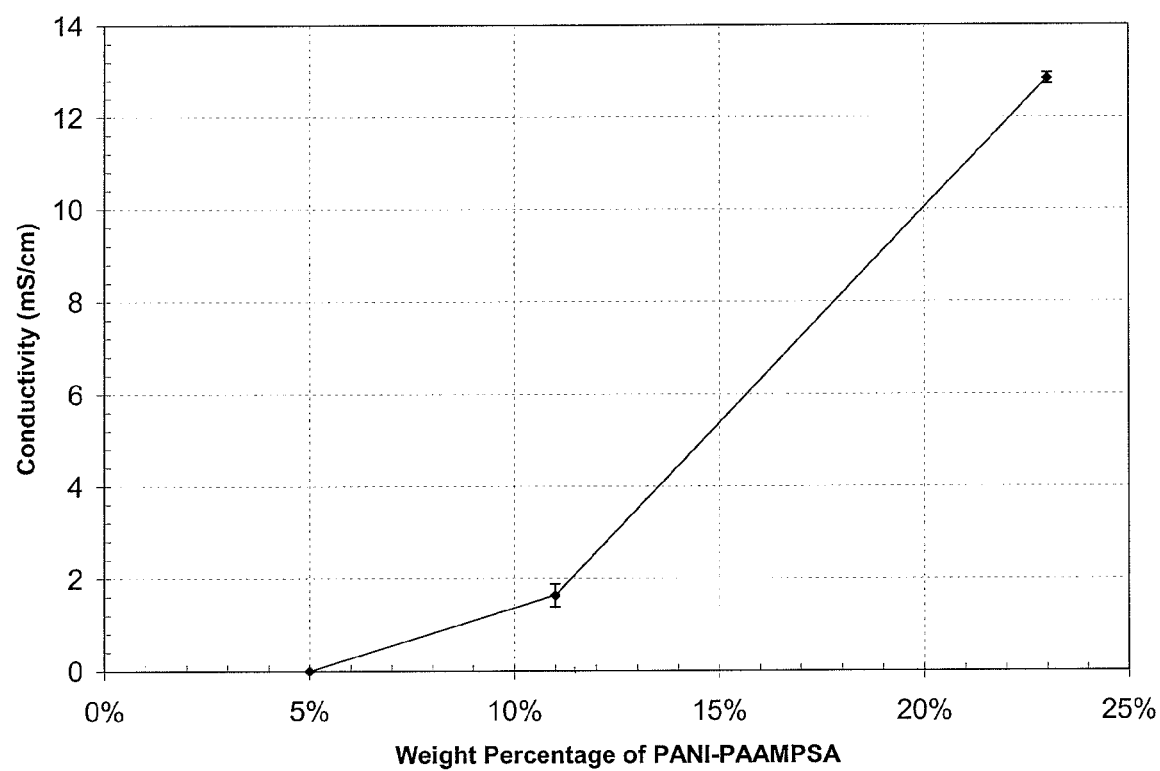
FIG. 4 illustrates the conductivity of a film of PANI-semi IPN recognitive hydrogel as a function of weight percentage of PANI-PAAMPSA, according to an embodiment of the present invention.
Figure 5:
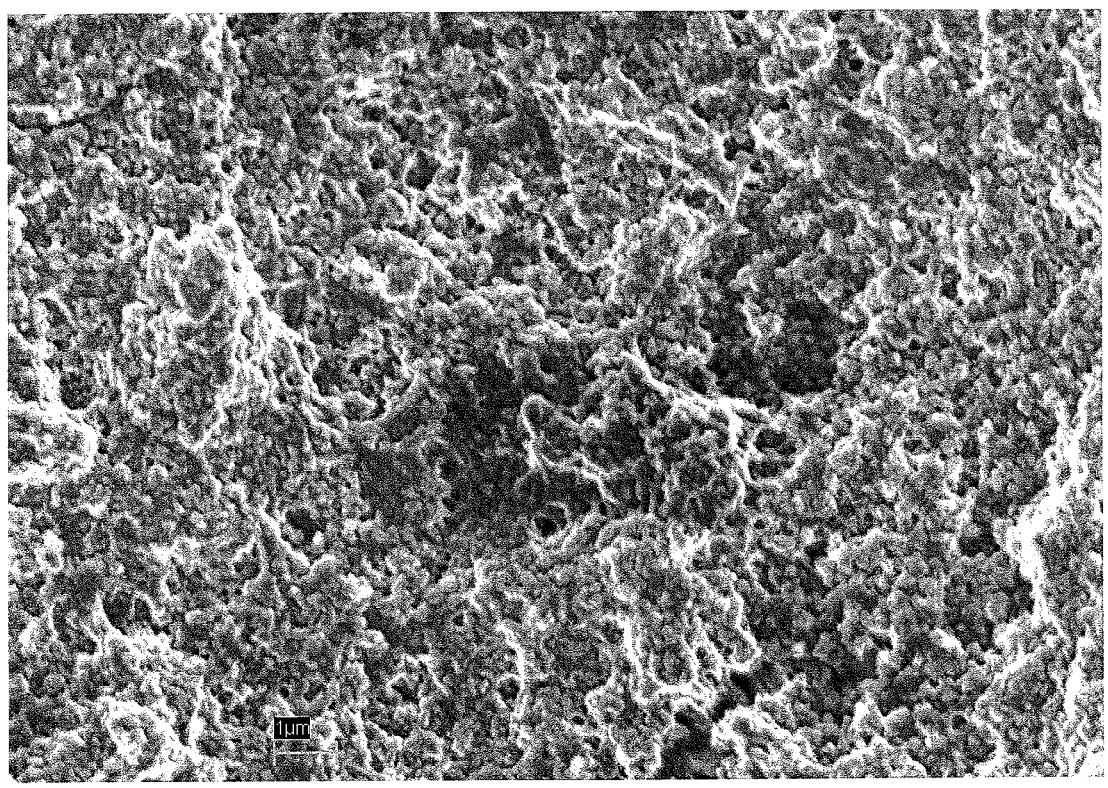
FIG. 5 shows a scanning electron microscopy image of the surface of a film of PANI-semi IPN recognitive hydrogel, according to an embodiment of the present invention.

The PANI-PAAMPSA recognitive hydrogel demonstrated conductive properties as measured by a four-point probe method and by UV-VIS spectroscopy. Spectroscopy results verifying the conductivity of the PANI-PAAMPSA in the film are shown in FIG. 3. The peak absorbance indicating the delocalized electron of the PANI material matches for both PANI-PAAMPSA films that are not blended with a CBIP, and PANI-PAAMPSA that is incorporated in an CBIP-containing recognitive hydrogel film. Additionally, as the weight percentage of PANI-PAAMPSA in the hydrogel film is increased, the conductivity measured using a four-point probe also increases, as shown in FIG. 4. A scanning electron microscopy image of the conductive polymer distributed in the hydrogel network is shown in FIG. 5.

Example 2

PANI pH Response

In addition, thin films of PANI-PAAMPSA alone were obtained by spin coating the PANI-PAAMPSA in a water solution onto cleaned glass substrates at 500 RPM for 60 seconds. In this case, the water is allowed to evaporate, leaving a thin conductive film of PANI-PAAMPSA on the glass substrate.

The resulting thin films were characterized. Conductivity of the recognitive hydrogel was verified using a 4-point probe and an Agilent 4145B Semiconductor Parameter Analyzer. Voltage was swept from −1V to +1V and the conductance was calculated. A Dektak II profilometer was used to measure the thickness of the film.

Figure 6:
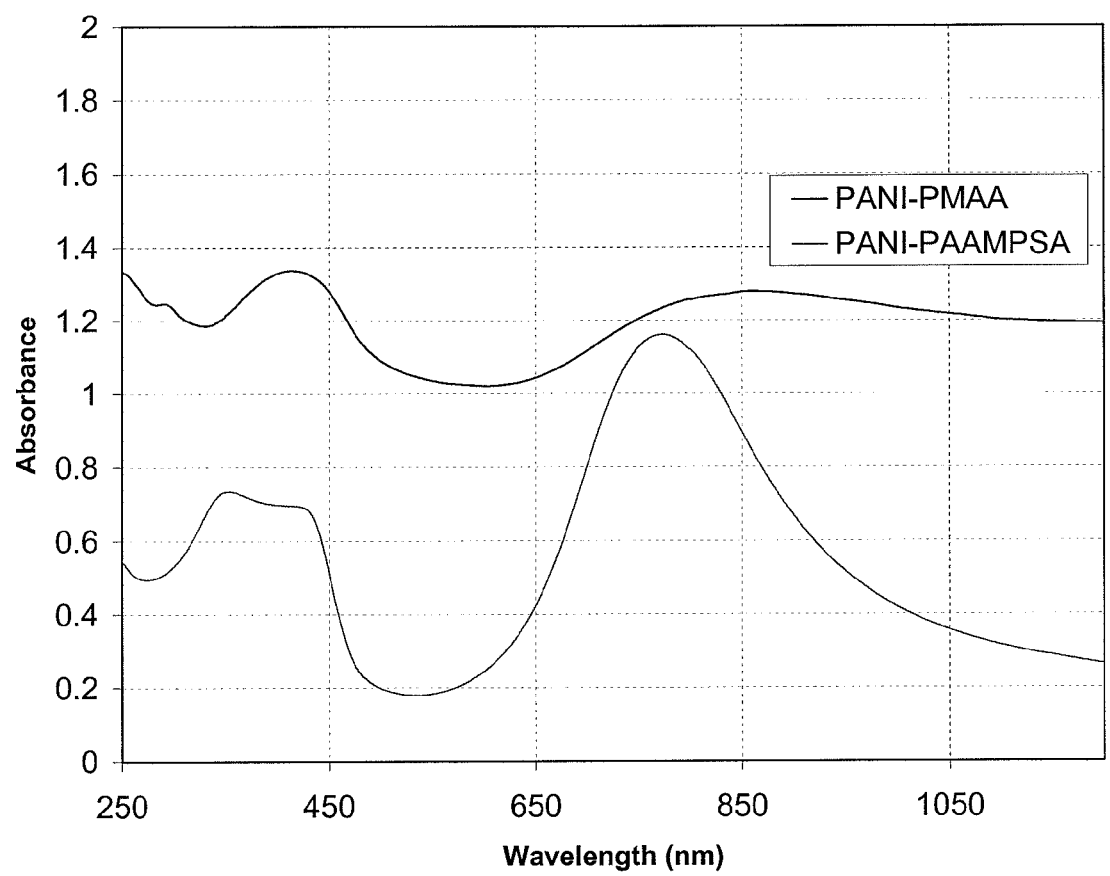
FIG. 6 illustrates the absorbance of a film of PANI-PMAA, according to an embodiment of the present invention.
Figure 7:
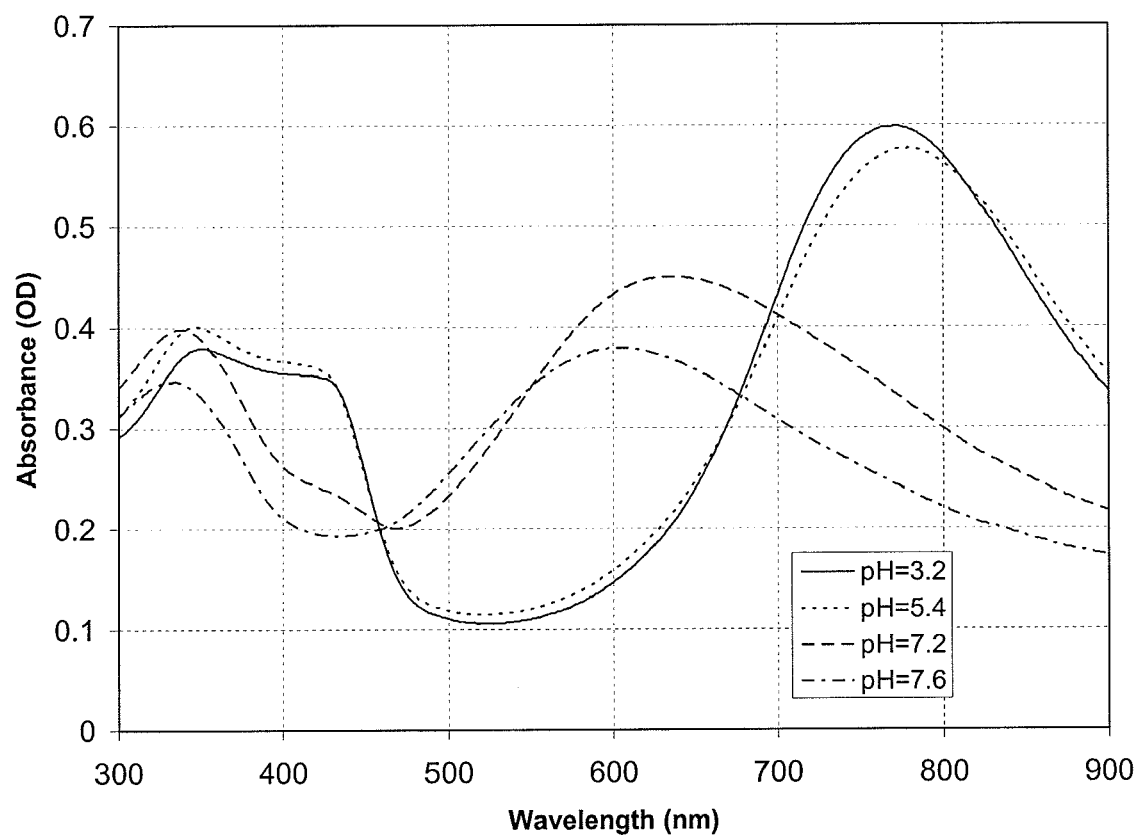
FIG. 7 illustrates the change in the absorbance of PANI-PAAMPSA with change in solution pH, according to an embodiment of the present invention.
Figure 8:
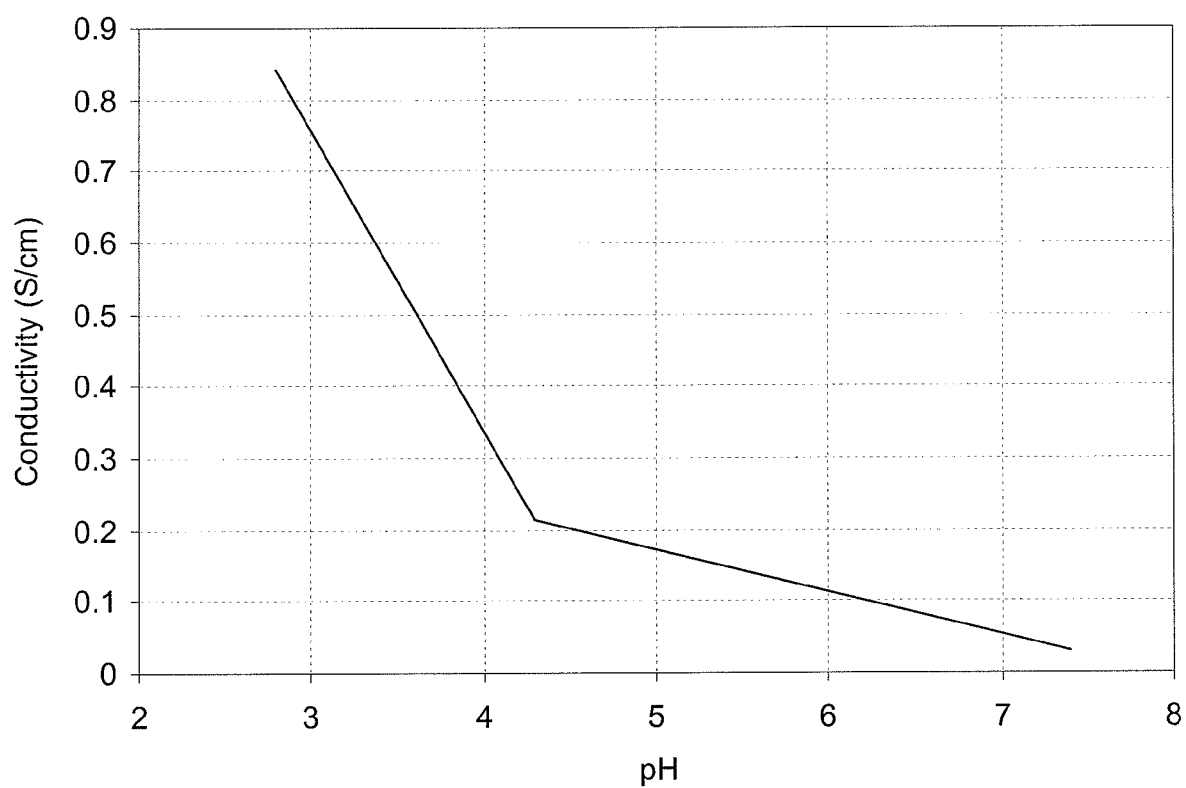
FIG. 8 illustrates the change in the conductivity of PANI-PAAMPSA with change in solution pH, according to an embodiment of the present invention.

To determine the sensing response of the PANI-PAAMPSA, the CP was dissolved in buffer at varying pH values. As before, the PANI-PAAMPSA was spun coat onto glass substrates and the conductivity of the resulting films was measured. Additionally, UV-VIS spectroscopy was used to measure the absorbance of the PANI-PAAMPSA solutions at the varying pHs. The spectroscopy results are shown in FIG. 6, while the conductivity results are shown in FIG. 7. It can be seen that the PANI-PAAMPSA de-dopes as the pH is increased. At high pHs, the absorbance spectra resembles that of the non-conductive emeraldine base form of PANI, while the conductivity decreases. Since the PAAMPSA allows the PANI to disperse in water, as the PANI is de-doped it will aggregate. As measured by dynamic light scattering, and shown in FIG. 8, the particle size of the PANI-PAAMPSA does increase with pH, indicating that the PAAMPSA is no longer doping the PANI and the PANI is aggregating as a result.

Example 3

PANI Biomolecular Response

Figure 9:
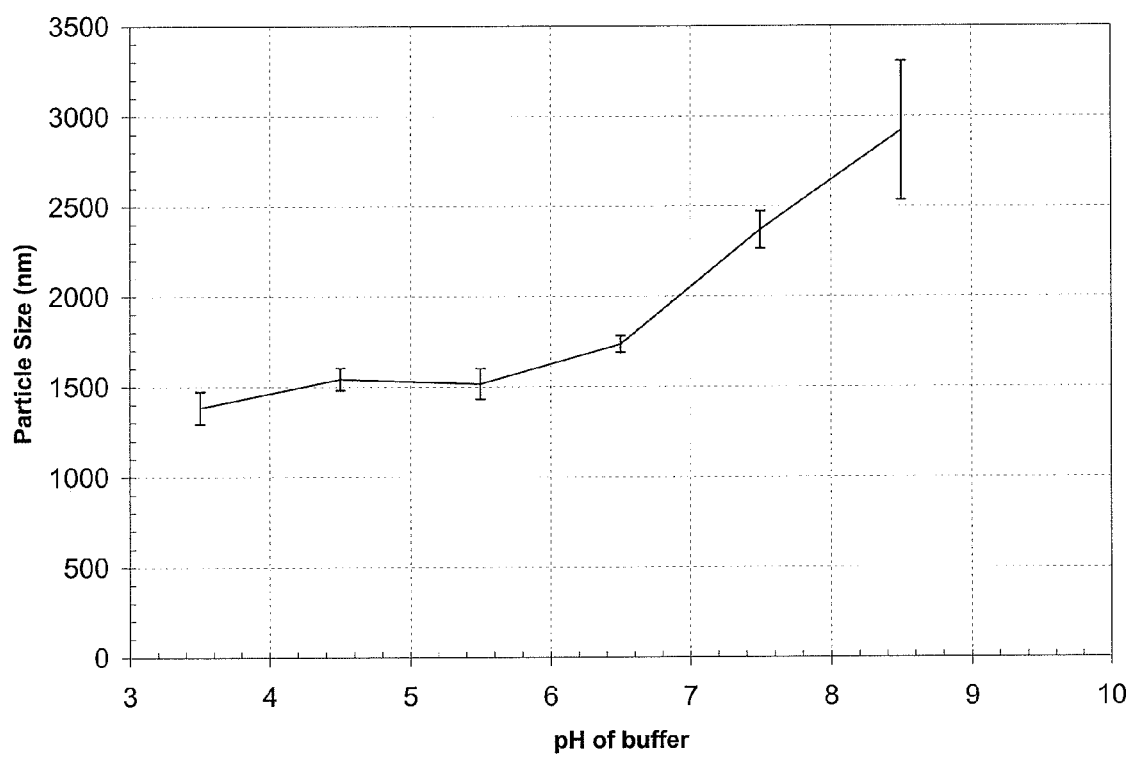
FIG. 9 illustrates the change in particle size of PANI-PAAMPSA with change in solution pH, according to an embodiment of the present invention.
Figure 10:
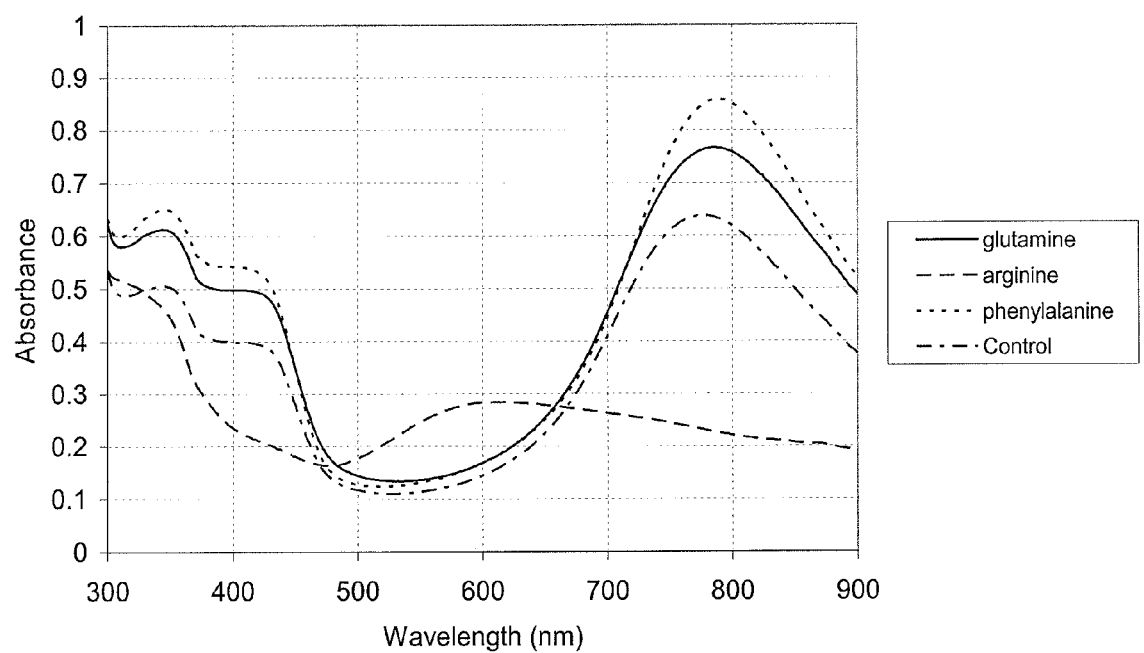
FIG. 10 illustrates the change in the absorbance of PANI-PAAMPSA in solution with amino acids, according to an embodiment of the present invention.
Figure 11:
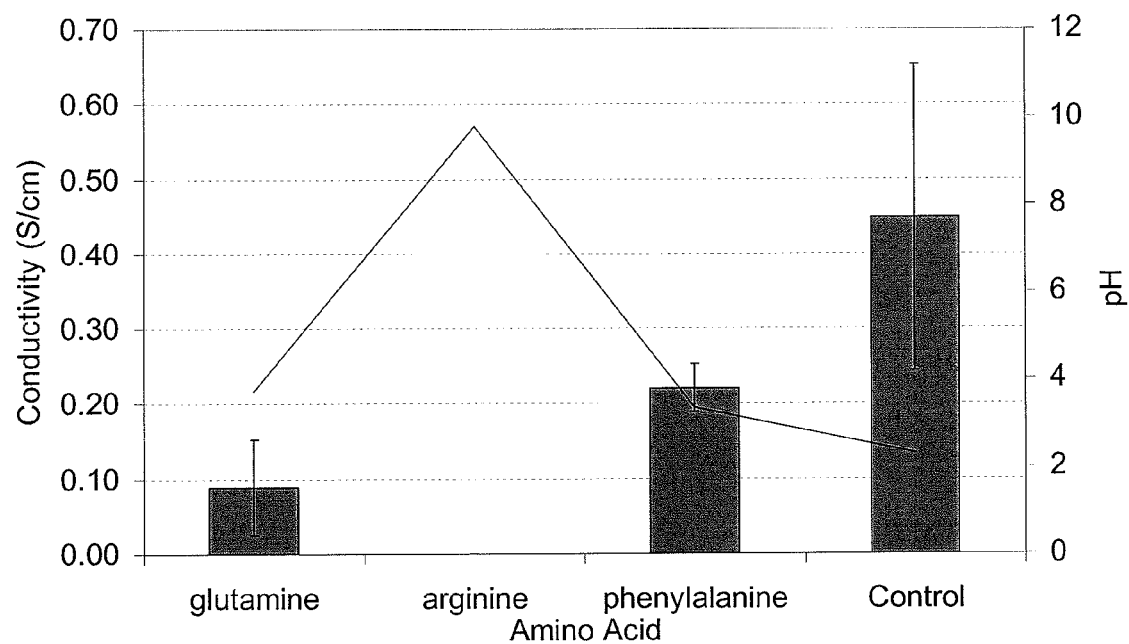
FIG. 11 illustrates the change in the conductivity of PANI-PAAMPSA with addition of amino acids, according to an embodiment of the present invention.

Similarly to the experiments described in Example 2 above, a PANI-PAAMPSA response to amino acids, proteins and peptides has been demonstrated. PANI-PAAMPSA was dissolved in water, then amino acids with specific functional characteristics were added to the solution. After incubation, thin films of the PANI-PAAMPSA were spun coat onto glass substrates and the conductivity and UV-VIS absorbance of the PANI-PAAMPSA was measured. The spectroscopy results in FIG. 9 and FIG. 10 demonstrate that the absorbance of the PANI-PAAMPSA does change in the presence of specific biomolecules. This absorbance can be correlated to the conductivity change shown in FIG. 11.

Example 4

PANI-PAAMPSA In Situ Film Response

Figure 12:
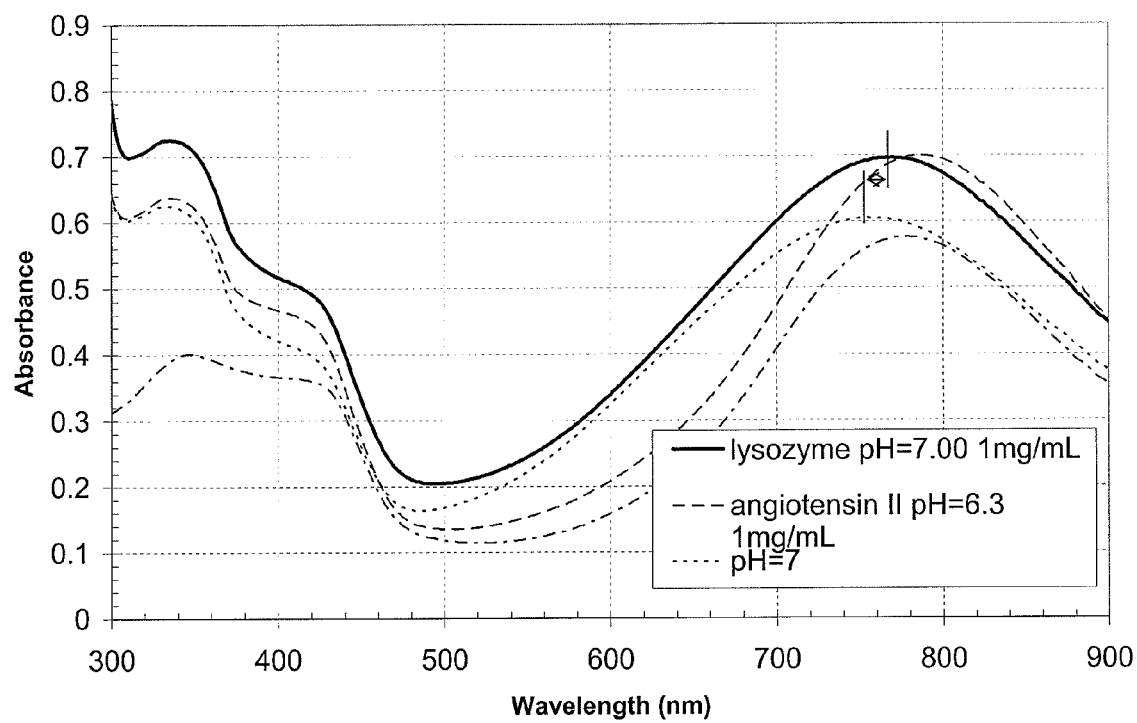
FIG. 12 illustrates the change in the absorbance of PANI-PAAMPSA in solution with a protein lysozyme, and a peptide, angiotensin II, according to an embodiment of the present invention.
Figure 13:
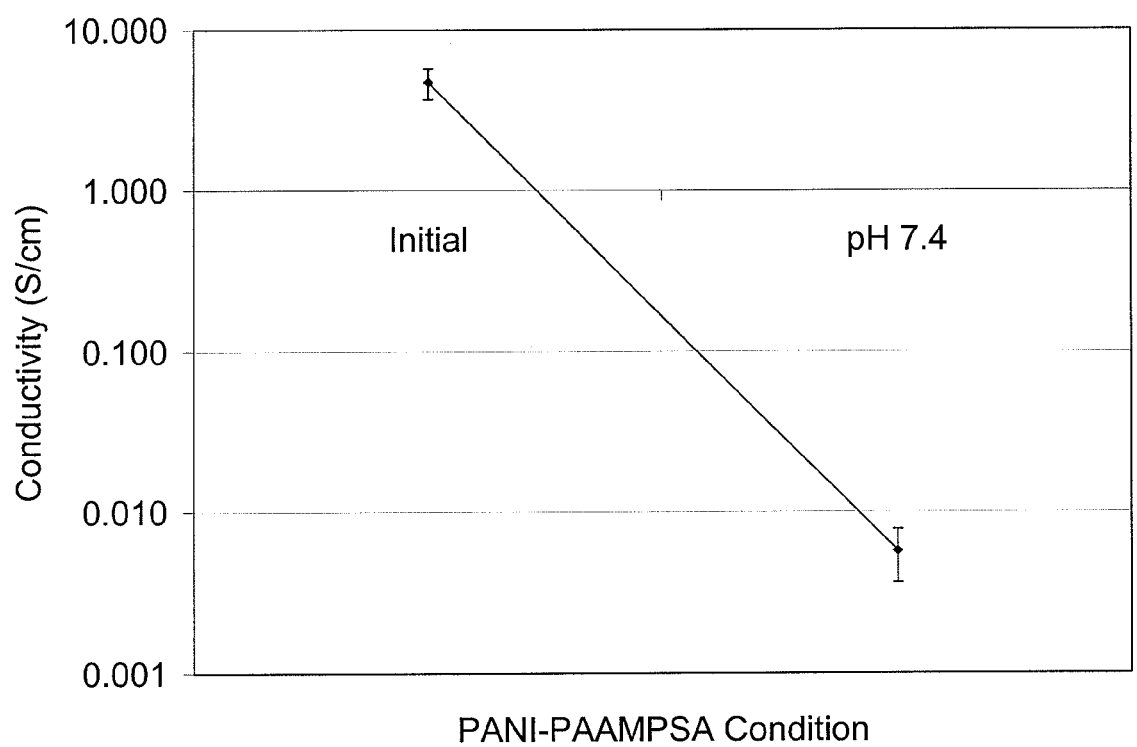
FIG. 13 illustrates the change in the conductivity of an absorbed nanofilm of PANI-PAAMPSA upon exposure to a buffered solution, according to an embodiment of the present invention.
Figure 14:
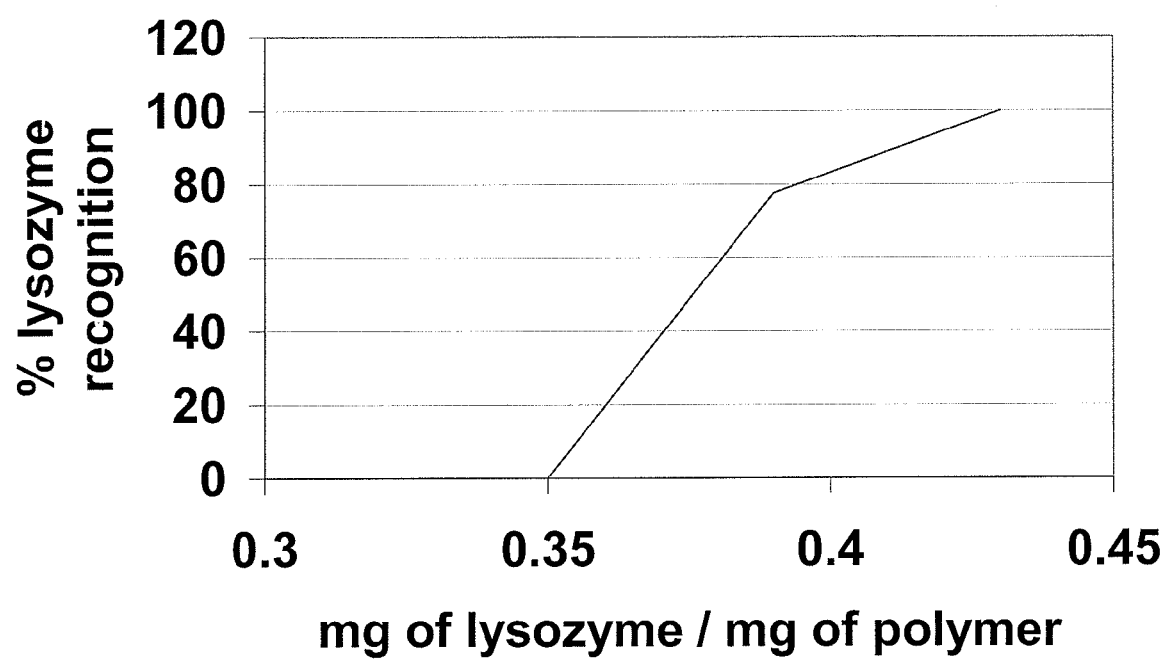
FIG. 14 illustrates the lysozyme recognitive properties of the hydrogel MIP, according to an embodiment of the present invention.

To determine the sensing response of the PANI-PAAMPSA in a film format, in situ polymerized films have been synthesized. Cleaned glass slides with thermally evaporated gold electrodes were exposed to the PANI-PAAMPSA reaction solution. Upon completion of the reaction, 50 to 120 nm thin films of PANI-PAAMPSA were adsorbed to the glass. These films can be rinsed in water, acetone, and various buffers, and they remain adsorbed to the glass substrate. These films were incubated in buffers at varying pHs, and the conductivity change of the film was measured using a four point probe technique. The conductivity of the films changed three orders of magnitude as the pH was increased to 7.4, compared to the films initial value when soaked in deionized water, as shown in FIG. 12.

Example 5

Further Hydrogel Testing

To determine the impact of the triggering biomolecule on the doping system of the conductive polymer, several experiments may be performed.

First, proteins and peptides with varying regions of electronegativity may be selected for comparison as triggering molecules.

Second, to determine the extent of interaction between the conductive polymer and the triggering biomolecule, the conductive polymer may be synthesized in the presence of a linear polymer acid which may be studied in solution. For example, methacrylic acid is a monomer that is frequently used in CBIPs and may be synthesized as a linear polymer and then used to dope PANI. UV-VIS spectroscopy of conductive polymers such as PANI may show the extent of doping of PANI. Measurement of the UV-VIS spectroscopy of the conductive polymer and dopant polymer complex in the presence of various triggering biomolecule will allow one to select those triggering biomolecule which demonstrate an interaction with the complex.

Third, these biomolecules may be imprinted on a recognitive hydrogel incorporating the polyacid and PANI, then the film may be exposed to varying concentrations of the triggering biomolecules and conductivity may be measured using a four-point probe technique.

Fourth, scanning electron microscopy, Fourier Transform Infrared spectroscopy, X-Ray diffraction spectra and solid state NMR may be used to determine structure and interactions of the final recognitive hydrogel.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A recognitive hydrogel comprising:
   a molecularly imprinted polymer having a binding cavity specific for a triggering molecule; and
   a conductive polymer associated with the molecularly imprinted polymer,
   wherein the molecularly imprinted polymer and the conductive polymer are associated by semi-interpenetrating network polymerization.

2. The recognitive hydrogel of claim 1, wherein the triggering molecule comprises at least one chemical group selected from the group consisting of: a carboxyl group; a hydroxyl group; an amino group; a carbonyl group; and a thiol group.

3. The recognitive hydrogel of claim 1, wherein the triggering molecule comprises a biomolecule.

4. The recognitive hydrogel of claim 1, wherein the triggering molecule comprises at least one molecule selected from the group consisting of: a protein; a polypeptide; and a peptide.

5. The recognitive hydrogel of claim 1, wherein the triggering molecule comprises at least one molecule selected from the group consisting of: a monosaccharide; an oligosaccharide; and a polysaccharide.

6. The recognitive hydrogel of claim 1, wherein the triggering molecule comprises a molecular decoy.

7. The recognitive hydrogel of claim 1, wherein the molecularly imprinted polymer comprises a configurationally biomimetic imprinted polymer.

8. The recognitive hydrogel of claim 1, wherein the molecularly imprinted polymer comprises at least one monomer selected from the group consisting of: acrylic acid; methacrylic acid; ethacrylic acid; propacrylic acid; an acrylate; a methacrylate; an acrylamide; and any derivative thereof.

9. The recognitive hydrogel of claim 1, wherein the molecularly imprinted polymer comprises at least one crosslinking agent selected from the group consisting of: ethylene glycol dimethacrylate; diethylene glycol dimethacrylate; triethylene glycol dimethacrylate; tetraethylene glycol dimethacrylate; poly(ethylene glycol dimethacrylate); and any derivative thereof.

10. The recognitive hydrogel of claim 1, wherein the conductive polymer comprises at least one polymer selected from the group consisting of: polyaniline; polypyrrole; any derivative thereof; and any copolymer thereof.

11. The recognitive hydrogel of claim 1, wherein the molecularly imprinted polymer and the conductive polymer are associated by non-covalent interactions.

12. The recognitive hydrogel of claim 1, wherein the molecularly imprinted polymer provides charge transport properties to the conductive polymer.

13. The recognitive hydrogel of claim 1, further comprising more than one molecularly imprinted polymer.

14. The recognitive hydrogel of claim 13, wherein each molecularly imprinted polymer comprises a binding cavity specific to a different triggering molecule.

15. The recognitive hydrogel of claim 1, wherein the molecularly imprinted polymer changes conformation when exposed to the triggering molecule.

16. A sensor comprising:
a recognitive hydrogel comprising:
    a molecularly imprinted polymer having a binding cavity specific for a triggering molecule; and
    a conductive polymer associated with the molecularly imprinted polymer, wherein the molecularly imprinted polymer and the conductive polymer are associated by semi-interpenetrating network polymerization; and
an impedance sensing component.

17. The sensor of claim 16, wherein the sensor further comprises at least one element selected from the group consisting of: a film on a silicon wafer; a microcantilever; a glass slide; a polymer film; a polymer substrate; and a biodegradable polymer substrate.

18. The sensor of claim 16, wherein the recognitive hydrogel is in a pattern formed by spatial control of patterning.

19. A method comprising:
providing a sensor comprising:
    a recognitive hydrogel that comprises a molecularly imprinted polymer having a binding cavity specific for a triggering molecule and a conductive polymer associated with the molecularly imprinted polymer; and
    an impedance sensing component;
allowing the triggering molecule to bind to the molecularly imprinted polymer so as to produce a non-electrochemical signal that changes the impedance of the recognitive hydrogel; and
detecting the change in impedance of the recognitive hydrogel with the impedance sensing component.

20. The method of claim 19, wherein the non-electrochemical signal comprises a change in the doping of the conductive polymer.

21. The method of claim 19, wherein the binding of the triggering molecule to the molecularly imprinted polymer results in a conformation change of the molecularly imprinted polymer.

22. The method of claim 19, wherein the non-electrochemical signal comprises a change in hydrophilicity or hydrophobicity of the recognitive hydrogel.

* * * * *